United States Patent [19]
Sunkara

[11] Patent Number: 5,865,971
[45] Date of Patent: Feb. 2, 1999

[54] SEALING RING WITH ELECTROCHEMICAL SENSING ELECTRODE

[75] Inventor: Mahendra K. Sunkara, Louisville, Ky.

[73] Assignee: Faraday Technology, Inc., Clayton, Ohio

[21] Appl. No.: 822,706

[22] Filed: Mar. 21, 1997

Related U.S. Application Data

[60] Provisional application No. 60/013,859, Mar. 22, 1996.

[51] Int. Cl.[6] ................................................. G01N 27/26
[52] U.S. Cl. .......................... 204/404; 204/280; 204/412; 277/602; 277/608; 277/614; 277/910; 277/919
[58] Field of Search .................................... 204/404, 196, 204/197, 412, 280, 416, 433; 277/602, 608, 614, 910, 919

[56] References Cited

U.S. PATENT DOCUMENTS

| | | | |
|---|---|---|---|
| 3,094,337 | 6/1963 | Pippert et al. | 277/178 |
| 3,788,654 | 1/1974 | Mandley | 277/229 |
| 4,090,029 | 5/1978 | Lundeberg | 174/51 |
| 4,453,723 | 6/1984 | Greenwald | 277/164 |
| 4,779,903 | 10/1988 | Maier et al. | 285/336 |
| 5,090,871 | 2/1992 | Story et al. | 417/9 |
| 5,121,929 | 6/1992 | Cobb | 277/2 |
| 5,246,235 | 9/1993 | Heinzen | 277/2 |
| 5,248,080 | 9/1993 | Stapleton | 228/175 |

*Primary Examiner*—Bruce F. Bell
*Attorney, Agent, or Firm*—Vorys, Sater, Seymour and Pease

[57] ABSTRACT

A sealing ring containing an electrode for sensing electrochemical conditions within a fluid handling system, in particular, the occurrence of crevice corrosion, has a body formed of a continuous loop of an electrically insulating fluid-impervious material having a surface which can form a fluid-tight seal with elements of a fluid handling apparatus, an electrode embedded within the body and electrically insulated from electronic conductive contact with those portions of the surface of the body that contact the fluid handling apparatus, and channels extending between the electrode and the surface of the body of the sealing ring to permit electrochemical contact between the electrode and the fluid within the system. The sealing ring also includes electronically conductive wires to connect the embedded electrode to external electrical devices, e.g., electronic measuring equipment.

14 Claims, 6 Drawing Sheets

FIG. 1
FIG. 2
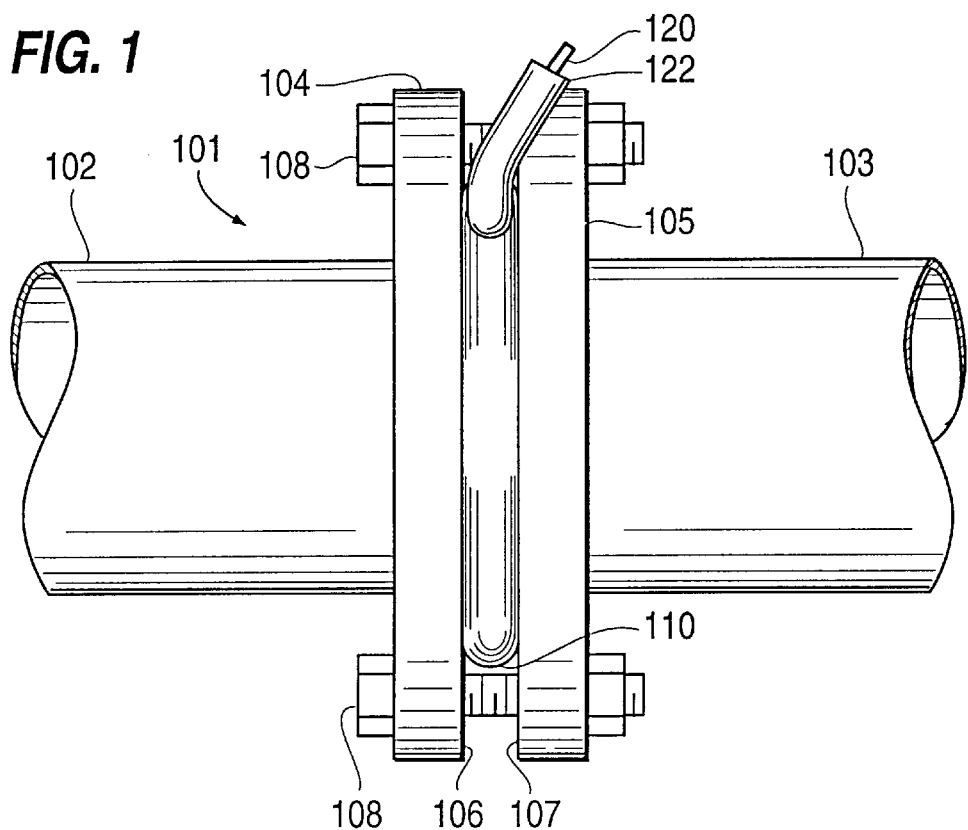
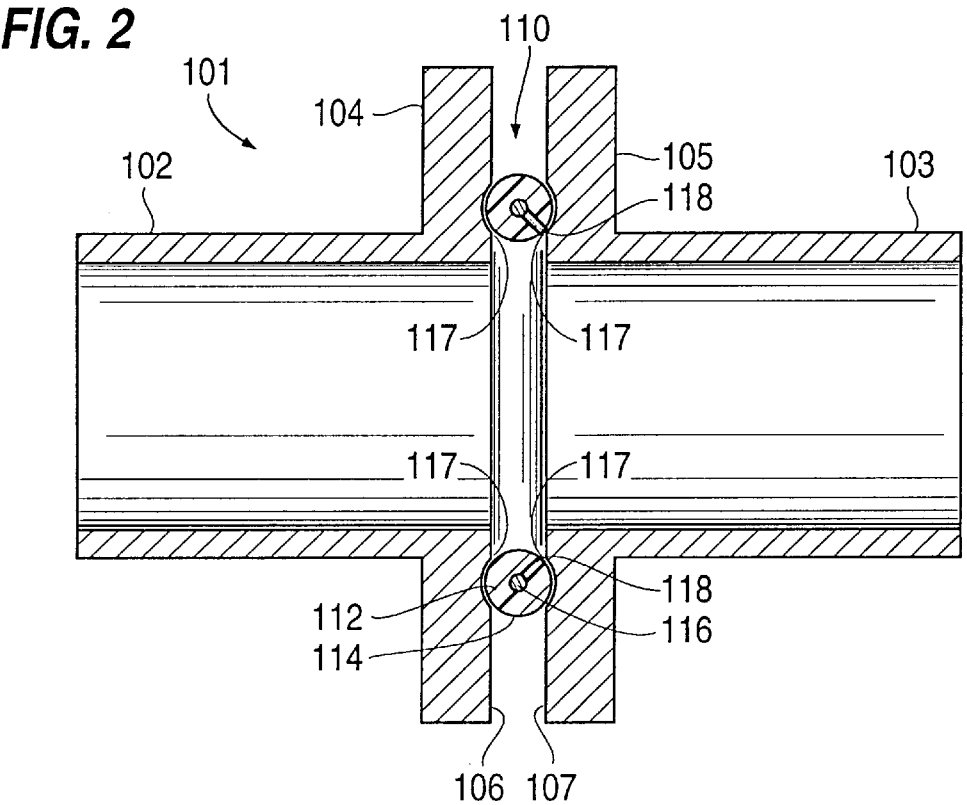

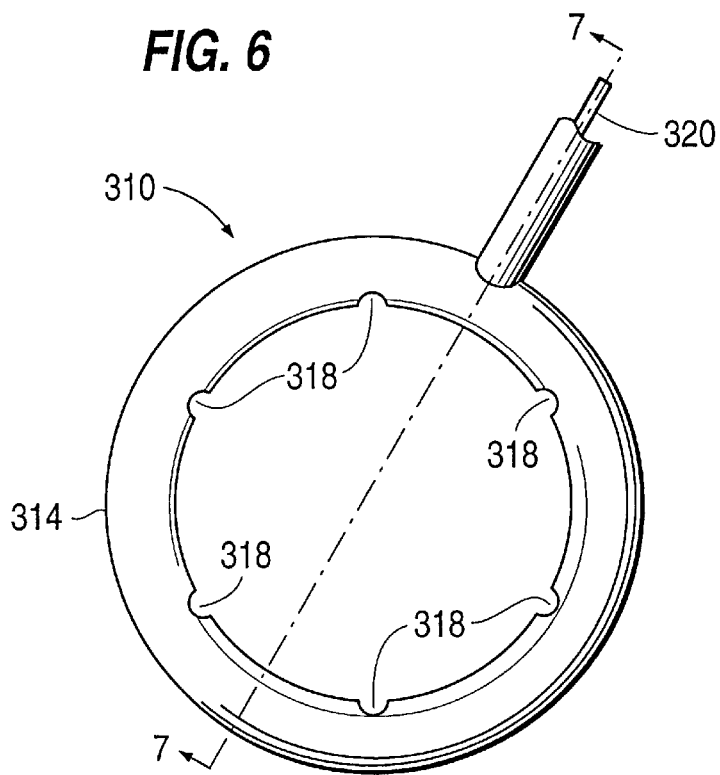
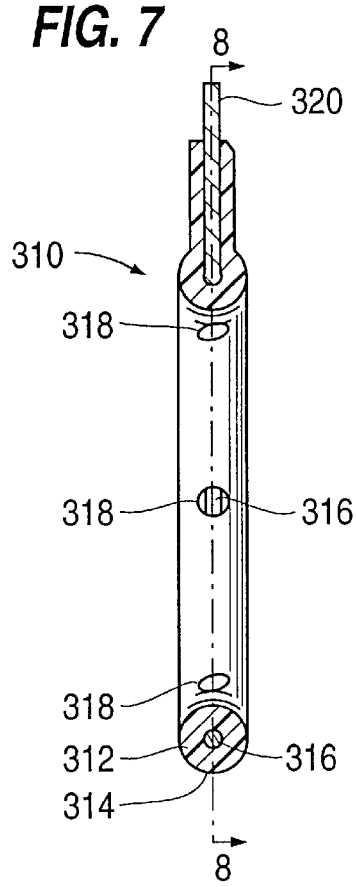
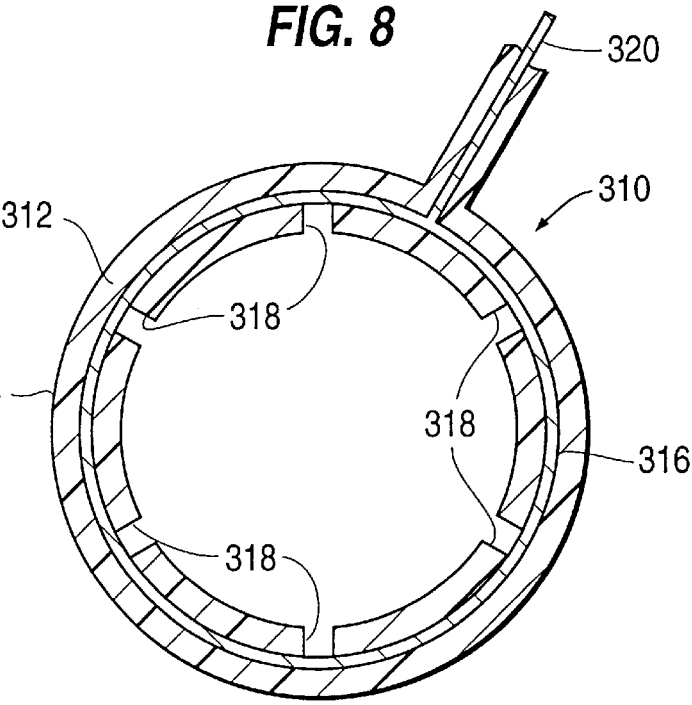

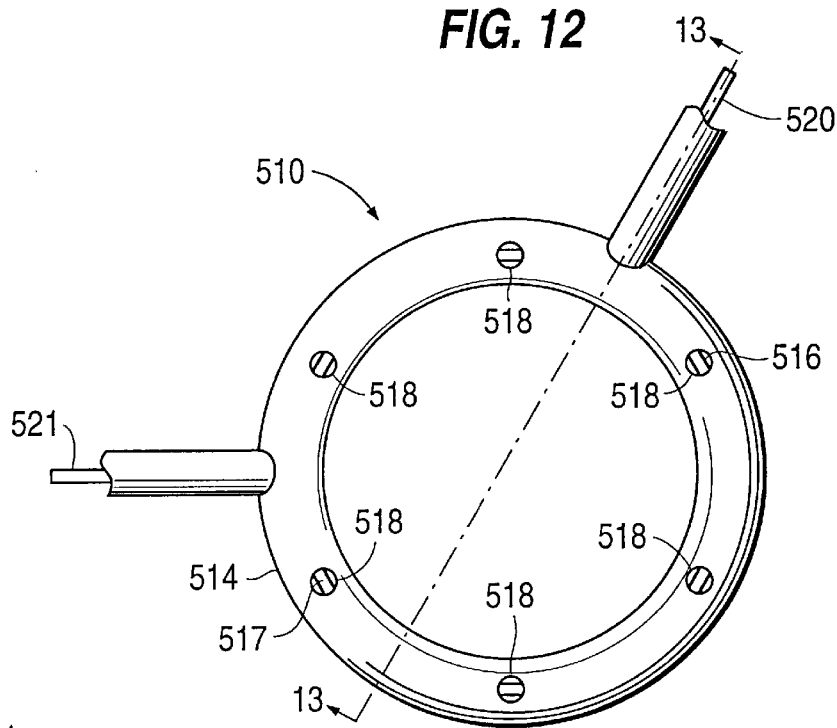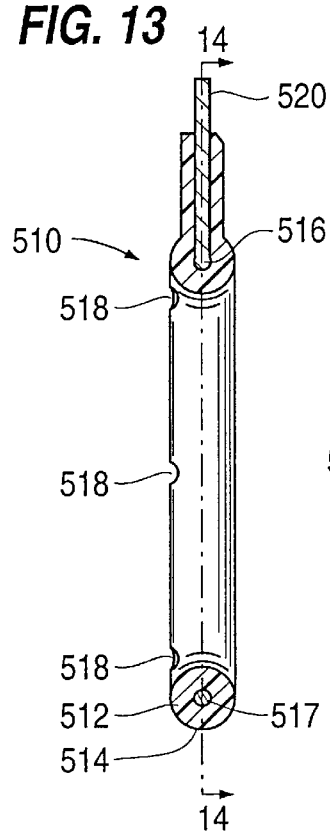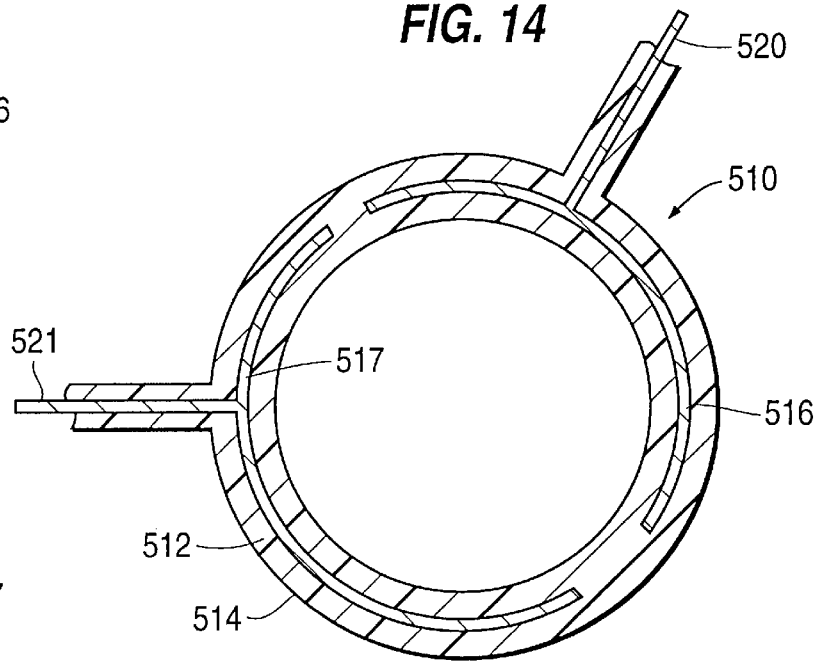

SEALING RING WITH ELECTROCHEMICAL SENSING ELECTRODE

ORIGIN OF THE INVENTION

The experimental work leading to this invention was funded in part by the Office of Naval Research SBIR Phase II Contract #N00014-94-C-0136.

This application claims the benefit of U.S. Provisional Application No. 60/013,859 filing date Mar. 22, 1996.

BACKGROUND OF THE INVENTION

1. Field of the invention

This invention relates to sealing rings for fluid conduits and more particularly to leasing rings incorporating electrochemical sensing electrodes.

2. Brief Description of the Prior Art

Electrochemical measurements relating to fluids contained inside sealed containers or piping systems would be of value to determine the properties of the fluids and to detect changes in the properties of the fluid that might indicate corrosion of the container or pipes. Such measurements require an electrochemical sensing electrode in contact with the solution within the sealed system. Such contacts could be provided by a simple through-wall fitting that supports an electrochemical electrode in contact with the fluid and provides an insulated electrical conductor extending through the wall of the fluid containment vessel.

In most circumstances, however, the use of conventional through-wall fittings is disadvantageous and ineffective. In the case of fluid handling systems that must be of the highest integrity, e.g., in nuclear reactor facilities or in naval vessels such as submarines, it is preferred to have as few apertures as possible in the fluid handling systems because each such aperture is considered a weak point that may compromise the integrity of the system. Furthermore, special elements with electrochemical fittings introduce complexity into the system because, e.g., a special pipe segment incorporating such a fitting must be installed, and inventories of such special pipe segments must be maintained.

Another situation in which a conventional through-wall electrode fitting is disadvantageous is in the sensing of crevice corrosion that may be occurring within the fluid handling system. Crevice corrosion occurs in liquid-filled small cracks in the metallic components of the fluid handling system or in the fluid-filed interstices that occur in the couplings between parts of the system, e.g., at flanged pipe joints. Such corrosion afflicts even alloys that are highly resistant to corrosion in bulk, e.g., stainless steel or the Inconel® series alloys. Furthermore, because the crevice corrosion phenomenon is not well understood, it is difficult to predict when and where it will occur. At present, the only reliable method of detecting crevice corrosion is periodic inspection of the fluid handling system, which ordinarily requires draining and disassembly. In view of the great expense entailed by such inspection, alternative methods of detecting crevice corrosion have been sought. It has been found that corrosion at the surface of a metallic member immersed in a fluid can be detected electrochemically by monitoring the complex electrical impedance between the surface of the article to be inspected and a test electrode located in the fluid close to that surface. Such measurements have become conventional for monitoring corrosion in research. They can also be used to detect crevice corrosion, but the electrode must be located close to the location at which the crevice corrosion is occurring. Accordingly, to detect crevice corrosion occurring at flanged joints incorporating a sealing ring (O-ring) where the corrosion may be occurring in the narrow regions where the sealing ring is compressed against the face of the flange, it would be necessary to provide special flanges with fittings for mounting an electrode in contact with the thin layer of fluid found between the flanges. The design and implementation of such fittings adds considerable complexity and expense to the fluid handling system. The extra fitting is also a potential place for leakage, and, in fact, introduces another discontinuity in the wall of the system which may itself be a location for crevice corrosion.

Accordingly, a need has continued to exist for a simple means of inserting an electrode into a sealed fluid handling system, e.g., a piping system, in close proximity to locations in the piping system that are subject to crevice corrosion.

SUMMARY OF THE INVENTION

This problem has now been solved by the sealing ring of this invention which comprises a body comprising a continuous loop of an electrically insulating fluid-impervious material, the body of the sealing ring having a surface with at least a portion thereof adapted to form a fluid-tight contact with a fluid-confining surface of a fluid-containing apparatus, and having embedded within the body of the ring an electrode electrically insulated from electronic conductive contact with those portions of the surface of the body that contact the fluid-confining surfaces, the sealing ring being provided with channels between the electrode and the exterior surface of the body of the sealing ring to permit electrochemical contact between the electrode and the fluid within the system and electronically conductive means to connect the electrode to external electrical equipment.

Accordingly, it is a object of the invention to provide a sealing ring for fluid-containing apparatus that is equipped with an electrode.

A further object is to provide a sealing ring for fluid-containing apparatus having an embedded electrode.

A further object is to provide a sealing ring capable of providing an electrochemical connection to a fluid in a confined region of a fluid coupling joint.

Further objects of the invention will become apparent from the description of the invention which follows.

BRIEF DESCRIPTION OF THE DRAWINGS

FIG. 1 is an illustration of a fluid coupling incorporating a sealing ring of the invention.

FIG. 2 is an elevational cross-section of the fluid coupling illustrated in FIG. 1.

FIG. 6 is a plan view of another embodiment of a sealing ring according to the invention, adapted for measurement of properties of the liquid adjacent to the sealing ring.

FIG. 7 is a cross-section of the sealing ring of FIG. 6 along the line 7—7.

FIG. 8 is a cross-section of the sealing ring of FIGS. 6 and 7 taken along the line 8—8 in FIG. 7.

FIG. 12 is a plan view of another embodiment of a sealing ring according to the invention, incorporating a reference electrode and a counter electrode.

FIG. 13 is a cross-section of the sealing ring of FIG. 12 along the line 13—13.

FIG. 14 is a cross-section of the sealing ring of FIGS. 12 and 13 taken along the line 14—14 in FIG. 13.

DETAILED DESCRIPTION OF THE INVENTION AND PREFERRED EMBODIMENTS

Figure 3:
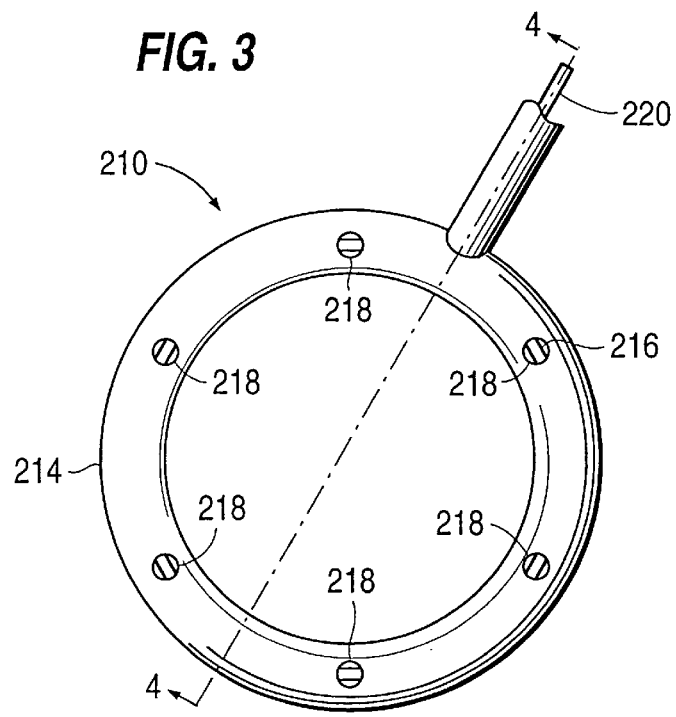
FIG. 3 is a plan view of a sealing ring according to the invention, adapted for detection of crevice corrosion at the metal surface adjacent to the sealing ring.

The sealing ring of the invention provides an apparatus that combines the function of sealing an aperture in a fluid-containing apparatus or system and providing a means of making electrochemical contact with the fluid within the apparatus. The sealing ring of the invention is suitable for use with any fluid-containing system that requires a fluid-tight seal between assembled parts of the apparatus. For example, in a system of pipes for transferring fluid from one location to another it is necessary to seal the joints in the piping system. Frequently such joints or couplings are provided with sealing rings such as O-rings compressed between bolted flanges. Portions of the exterior surface of the sealing ring contact the fluid-confining surfaces of the apparatus, e.g., the interior surfaces of the flanges, to form a fluid tight seal.

In order to provide an electrical method of assessing the properties of the fluid in the fluid-containing apparatus or the condition of the interior fluid-confining surfaces of the apparatus, an electrochemical circuit must be provided wherein external electrical measuring equipment can be connected to the internal fluid at selected locations, in particular at locations subject to crevice corrosion. Such apparatus requires electronic conduction between the electrical measuring apparatus and an electrode in contact with the fluid and electrochemical or ionic conduction between the electrode and the fluid or interior surfaces of the apparatus.

In order to provide an electrochemical contact with the fluid within such a fluid-containing apparatus, e.g., a piping system, the sealing ring of the invention incorporates an electrode that is electrically isolated or insulated from electronic conductive contact with those portions of the exterior surface of the sealing ring that contact the fluid-containing apparatus. Preferably the electrode is embedded within the body of the electrode and spaced from the exterior surface. The sealing ring is also provided with apertures or channels extending from the exterior surface of the ring to the electrode which can provide for the necessary ionic or electrochemical contact with the fluid within the apparatus. The channels may be openings that become filed with the confined fluid or may be filled with a solid material that allows for ionic conduction, e.g., an ion exchange resin.

The invention will now be described with reference to the figures of the drawings, wherein the reference numerals refer to the same elements throughout.

FIG. 1 illustrates a fluid coupling 101 of the type wherein the sealing ring of the invention may be advantageously employed. A first fluid conduit 102 having a flange 104 and a second conduit 103 having a flange 105 are coupled by bolting the flanges 104 and 105 together with a plurality of bolts 108 of which two are shown. A sealing ring 110 according to the invention is clamped between the faces 106 and 107 of the flanges 104 and 105. FIG. 2 shows an elevational cross-section of the fluid coupling of FIG. 1. The sealing ring 110 has a body 112 having a surface 114 and is formed of an electrically insulating fluid-impermeable resilient material suitable for forming a fluid-tight seal where the surface 114 comes into contact with the flanges 104 and 105. An electrode 116 is positioned within the body 112 of the sealing ring 110 in spaced relationship with the surface 114 of the sealing ring 110. Accordingly, the electrode 116 is not in electronic conductive contact with the flanges 104 and 105 of the fluid coupling 101. In such a fluid coupling 101, crevices, indicated generally by reference numeral 117, are necessarily formed where the sealing ring 110 contacts the faces 106 and 107 of the flanges 104 and 105. In order to monitor the electrochemical condition of the metal surface in the crevices 117, channels 118 are formed in the sealing ring 110 to permit ionic conductive contact between the electrode 116 and the crevice regions 117. The channels 118 may be open or filled with an ionically conducting solid such as an ion exchange resin. If the channels are open they become filled with the fluid within the fluid handling system of which the fluid coupling 101 is a part. In either case the electrode is in ionic conductive contact with the fluid in the crevices 117 and the adjacent metal parts of the fluid coupling that may be subject to crevice corrosion. The electrode 116 is connected to external monitoring equipment through electronically conductive lead 120 which is also insulated from contact with the metal flanges of the fluid coupling 101 by insulation 122. If the flanges 104 and 105 are not compressed too closely together, the lead 120 can be led out between the flanges 104 and 105 as shown in FIG. 1. However, one skilled in the art will understand that if the flanges 104 and 105 have to be compressed too closely together for convenient egress of the lead 120 and insulation 122, one or both of the faces 106 and 107 of the flanges 104 and 105 may be grooved or recessed to make room for the lead 120 and insulation 122, or the lead 120 with insulation 122 may be brought out through a hole made in one of the flanges.

The external monitoring equipment, which does not form a part of this invention, may be of any type which can indicate the presence of crevice corrosion in crevices 117. For example, the electrode 116 may be an electrochemically inert electrode, e.g., a platinum, titanium, or carbon fiber electrode, and an alternating potential of varying frequency can be imposed between the electrode 116 and the metal portions of the fluid conduit 110 in order to measure the complex impedance of the electrical circuit including the crevice region 117 of the fluid coupling 101. Variations in the complex impedance may then be used to assess the corrosion status of the metal surface in the region of crevices 117 as is conventional in the art. Alternatively, the electrode 116 may be a pH-sensitive electrode, e.g., a silver-silver chloride electrode, an oxygen-sensing electrode, a conductivity sensing electrode, or the like, and the external equipment may measure the potential or current of the electrode in order to determine local changes of pH, oxygen concentration, or electrical conductivity, all of which have been implicated in the mechanism of crevice corrosion attack, in the crevices 117.

The body 112 of the sealing ring of the invention may be made from any conventional electrically insulating material used for sealing elements in fluid handling systems, For example, elastomers such as nitrile rubber, silicone rubber, and partially or completely fluorinated elastomers, e.g., fluorocarbon elastomers, are suitable materials.

Figure 4:
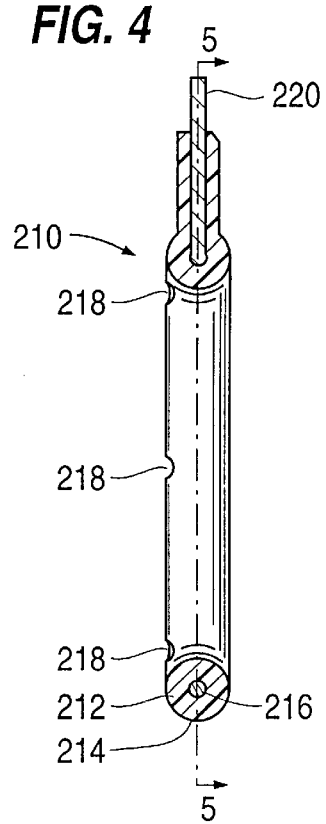
FIG. 4 is a cross-section of the sealing ring of FIG. 3 along the line 4—4.
Figure 5:
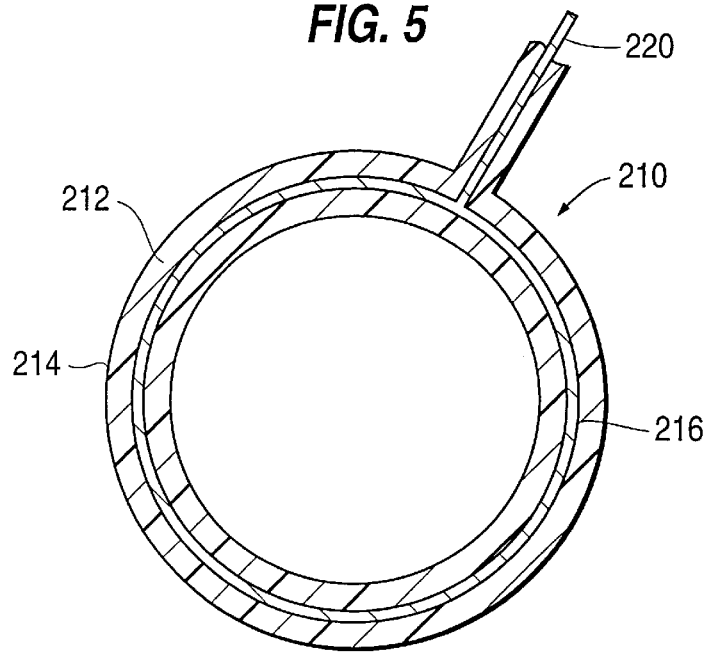
FIG. 5 is a cross-section of the sealing ring of FIGS. 3 and 4 taken along the line 5—5 in FIG. 4.

FIGS. 3–5 illustrate in more detail a sealing ring according to the invention. FIG. 3 shows a plan view of a sealing ring 210 of the invention, while FIGS. 4 and 5 show cross-sections of the ring 210. The sealing ring 210 has a body 212 having a surface 214. An electrode 216 is embedded within the body 212 spaced from the surface 214 so that it is electrically insulated from any electronic conductive contact with metal or other electronic conductor that may contact the surface 214. Channels 218 are formed in the body 212 extending from the surface 214 to the electrode 216. These channels 218 may be open or filled with an ionically conducting solid medium. The channels form an electronically conductive path between the electrode and the fluid in the crevices associated with the fluid coupling. An electronically conductive lead 220 connects the electrode 216 to external measuring equipment (not shown).

FIGS. 6–8 illustrate another embodiment of the sealing ring according to the invention. FIG. 6 shows a plan view of a sealing ring 310 of the invention, while FIGS. 7 and 8 show cross-sections of the ring 310. The sealing ring 310 has a body 312 having a surface 314. An electrode 316 is embedded within the body 312 spaced from the surface 314 so that it is electrically insulated from any electronic conductive contact with a metal or other electronic conductor that may contact the surface 314. Channels 318 are formed in the body 312 extending from the surface 314 to the electrode 316. These channels 318 may be open or filled with an tonically conducing solid medium. The channels form an ionically conductive path between the electrode and the fluid confined within the flanges of a fluid coupling such as the coupling 101 of FIG. 1. The sealing ring 314 is thus better adapted to measure bulk properties of the solution such as ionic concentration, pH and the like when the electrode 316 is of a type appropriate for measuring such properties. The choice of suitable electrodes for determining the value of a particular property of the solution is well known to a skilled electrochemical practitioner. An electronically conductive lead 320 connects the electrode 316 to external measuring equipment (not shown).

In some applications of the sealing ring of the invention it is advantageous to incorporate two or more electrodes into the sealing ring. For example, in complex impedance measurements that are used to detect crevice corrosion, the measurement may require the use of a reference electrode and a counter electrode.

Figure 9:
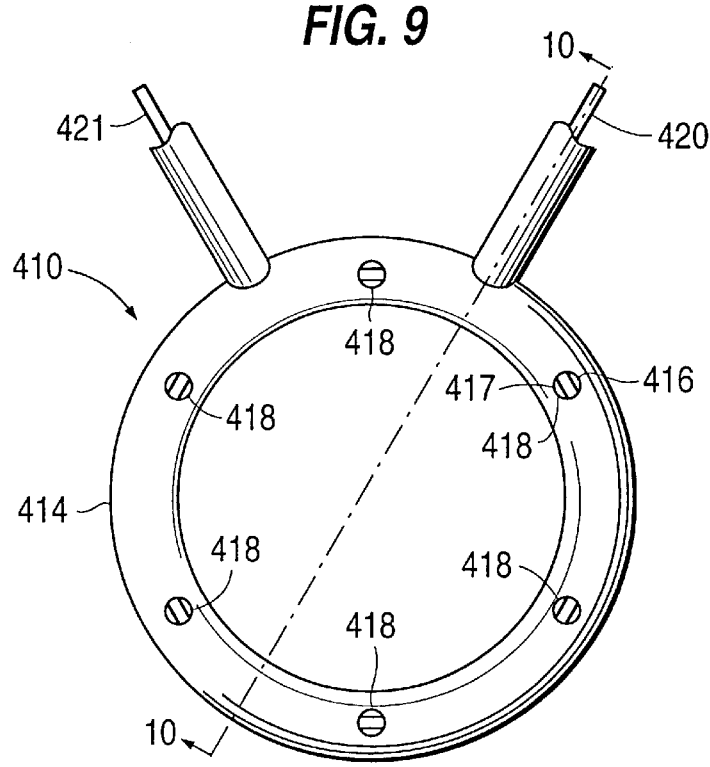
FIG. 9 is a plan view of another embodiment of a sealing ring according to the invention, incorporating a reference electrode and a counter electrode.
Figure 10:
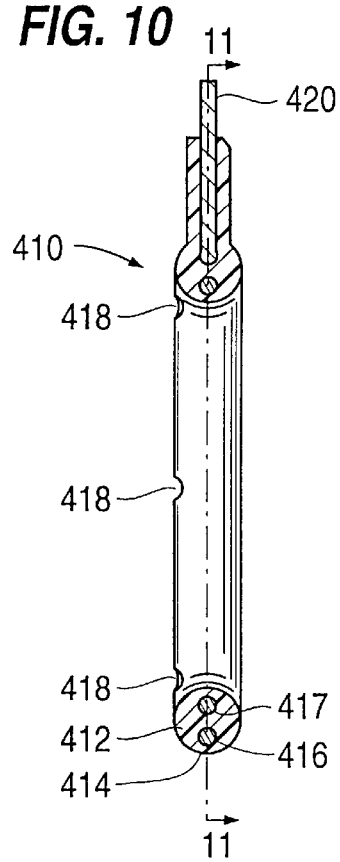
FIG. 10 is a cross-section of the sealing ring of FIG. 9 along the line 10—10.
Figure 11:
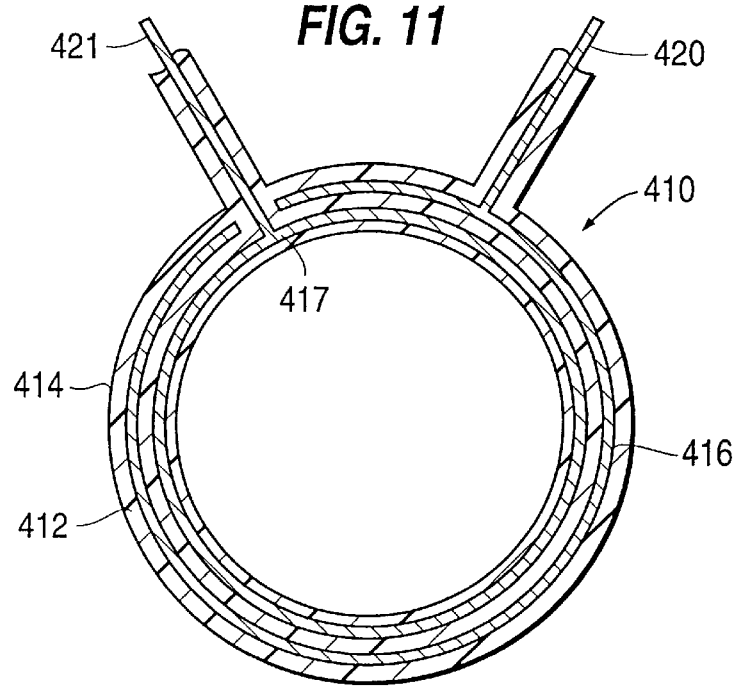
FIG. 11 is a cross-section of the sealing ring of FIGS. 9 and 10 taken along the line 11—11 in FIG. 10.

FIGS. 9–11 illustrate an embodiment of the sealing ring of the invention of the general type illustrated in FIGS. 3–5, but incorporating a reference electrode and a counter electrode. FIG. 9 shows a plan view of a sealing ring 410 according to this embodiment of the invention, while FIGS. 10 and 11 show cross-sections of the ring 410. The sealing ring 410 has a body 412 having a surface 414. A reference electrode 416 is embedded within the body 412 spaced from the surface 414 so that it is electrically insulated from any electronic conductive contact with a metal or other electronic conductor that may contact the surface 414. A counter electrode 417 is also embedded in the body 412 of the sealing ring 410 separated from the reference electrode 416 and insulated from any electronic electrical contact with the reference electrode 416, and also spaced from the surface 414. Channels 418 are formed in the body 412 extending from the surface 414 to the electrodes 416 and 417. These channels 418 form an ionically conductive path between both the reference electrode and the counter electrode and the fluid in the crevices associated with the sealing ring and adjacent metal surfaces. Electronically conductive leads 420 and 421 connect the electrodes 416 and 417 to external measuring equipment (not shown).

FIGS. 12–14 illustrate another embodiment of the sealing ring of the invention incorporating a reference electrode and a counter electrode. FIG. 12 shows a plan view of a sealing ring 510 according to this embodiment of the invention, while FIGS. 13 and 14 show cross-sections of the ring 510. The sealing ring 510 has a body 512 having a surface 514. A reference electrode 516 is embedded within the body 512 spaced from the surface 514 so that it is electrically insulated from any electronic conductive contact with a metal or other electronic conductor that may contact the surface 514. A counter electrode 517 is also embedded in the body 512 of the sealing ring 510 separated from the reference electrode 516 and insulated from any electronic electrical contact with the reference electrode 516, and also spaced from the surface 514. Channels 518 are formed in the body 512 extending from the surface 514 to the electrodes 516 and 517. The reference electrode 516 and the counter electrode 517 each extend around a different part of the circumference of the sealing ring 510 and each is exposed in those of the channels 518 in its part of the circumference. The channels 518 may be open or filled with an ionically conducting solid medium. The channels 518 form an ionically conductive path between both the reference electrode and the counter electrode and the fluid in the crevices associated with the sealing ring and adjacent metal surfaces. Electronically conductive leads 520 and 521 connect the electrodes 516 and 517 to external measuring equipment (not shown).

Figure 15:
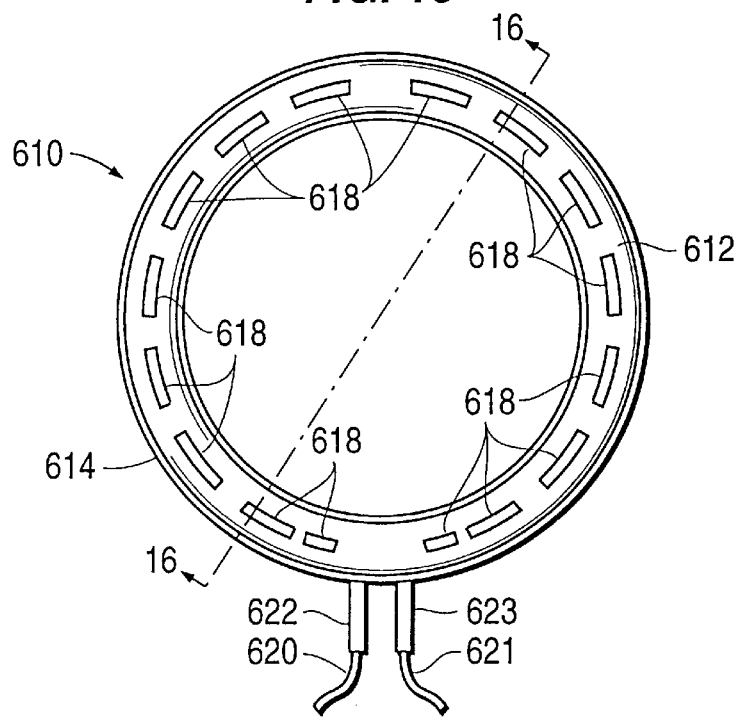
FIG. 15 is a plan view of another embodiment of a sealing ring according to the invention, incorporating a reference electrode and a counter electrode and incorporating slits in the body of the ring for allowing access of the surrounding fluid to the electrode.
Figure 16:
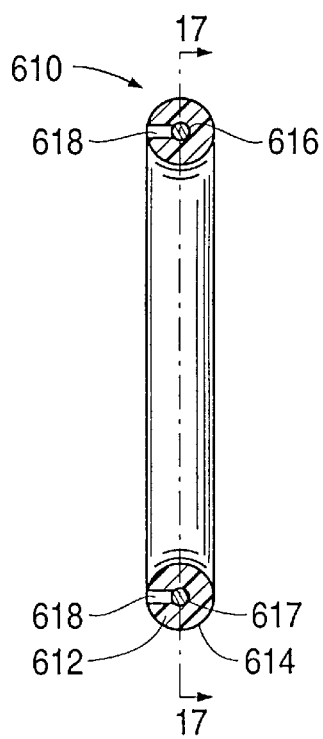
FIG. 16 is a cross-section of the sealing ring of FIG. 15 along the line 16—16.
Figure 17:
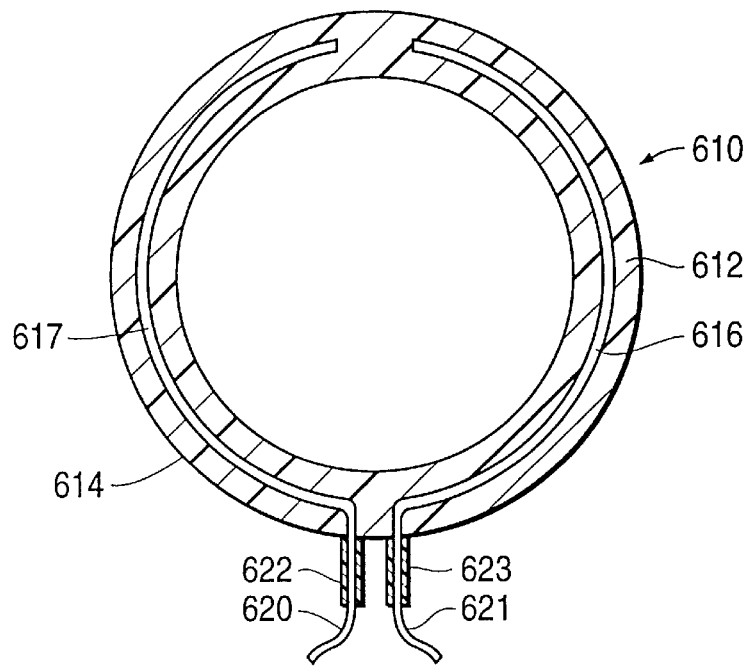
FIG. 17 is a cross-section of the sealing ring of FIGS. 15 and 16 taken along the line 17—17 in FIG. 16.

FIGS. 15–17 illustrate another embodiment of the sealing ring of the invention incorporating a reference electrode and a counter electrode with multiple slits in the body of the ring to provide access for the surrounding fluid to the electrodes. FIG. 15 shows a plan view of a sealing ring 610 according to this embodiment of the invention, while FIGS. 16 and 17 show cross-sections of the ring 610. The sealing ring 610 has a body 612 having a surface 614. A reference electrode 616 is embedded within the body 612 spaced from the surface 614 so that it is electrically insulated from any electronic conductive contact with a metal or other electronic conductor that may contact the surface 614. A counter electrode 617 is also embedded in the body 612 of the sealing ring 610 separated from the reference electrode 616 and insulated from any electronic electrical contact with the reference electrode 516, and also spaced from the surface 614. Multiple slits 618 are formed in the body 612 extending from the surface 614 to the electrodes 616 and 617. The reference electrode 616 and the counter electrode 617 each extend around a different part of the circumference of the sealing ring 610, and each electrode is exposed in those of the slits 618 in its part of the circumference. The slits 618 may be open or filled with an ionically conducting solid medium. The slits 618 are shown in the drawings as having a substantial width relative to the cross section of the O-ring, in order to illustrate the structure of the ring. Slits of such relative dimensions are useful. However, the slits 618 may also be very narrow, such as those made, for example by slicing slits in an integral O-ring with a sharp instrument such as a knife or the like. All that is required is that the slits 618 provide a means for establishing ionic conductive contact between the electrode and the fluid in contact with the surface 614 of the O-ring 610. Thus, any slit having a width sufficient to allow access of the surrounding fluid to the electrode is suitable. Similarly, the electrodes 616 and 617 are shown, for convenience in illustration, as having a substantial gauge and cross section. However, the electrodes 616 and 617 can be made of any gauge wire provided that a useful electrical contact between the electrode and the ionically conductive fluid in contact with the surface 614 of the O-ring 610 is established. Accordingly, the slits 618 provide an ionically conductive path between both the reference electrode and the counter electrode and the fluid in the crevices associated with the sealing ring and adjacent metal surfaces. Electronically conductive leads 620 and 621 connect the electrodes 616 and 617 to external measuring equipment (not shown). Short lengths of insulating tubing 622 and 623, e.g., heat-shrinkable tubing of poly (tetrafluoroethylene) (PTFE) are applied to the portions of the electrode leads 620 and 621 adjacent to the O-ring 610 in order to insulate the leads from possible contact with the adjacent metal parts of a fluid handling apparatus. The use of slits as means for access of fluid to the electrodes 616 and 617 allows a convenient method of preparing the rings of the invention by first molding a solid O-ring, then forming discontinuous slits such as those illustrated at 618 in the O-ring 610, and embedding the electrodes 616 and 617 in the body 612 of the ring 610 by threading the electrodes through the solid portions separating the slits, e.g., using a needle to draw the electrode wire through the body 614 of the O-ring 610.

Although the illustrated embodiments of the sealing ring of the invention show annular embodiments, it will be recognized by the skilled practitioner that the sealing ring of the invention may have other may have other planforms required for sealing non-circular openings or conduits in fluid handling systems. It is also according to the invention that a single sealing ring of the invention may be constructed to surround and seal a plurality of fluid conduits, e.g., adjacent conduits in a fluid handling system. Furthermore, although the illustrated embodiments of the invention comprise one or two electrodes, it will be recognized by those skilled in the art that more than two separate electrodes, each with its separate lead connecting it to external measuring equipment, can be incorporated into the sealing ring of the invention, for purposes of measuring different properties of the sealing ring environment or for more precisely identifying the location of crevice corrosion activity. Likewise, as many channels leading from the surface of the sealing ring to the embedded electrode may be introduced as may be necessary to provide good measurements of the sealing ring environment.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A sealing ring for use in fluid-containing apparatus, said sealing ring comprising:

a body comprising a continuous loop of an electrically-insulating fluid-impervious material, said body having an exterior surface, at least a portion of said exterior surface being adapted to contact a fluid-confining surface of a fluid-containing apparatus and form a fluid-tight contact with said fluid-confining surface of said fluid-containing apparatus;

an electrode, integral with said body, and electrically isolated from said portion of said exterior surface adapted to contact said fluid-confining surface of said fluid-containing apparatus; and means for providing electronic electrical contact between said electrode and an external electrical device;

said body being provided with channels extending between said electrode and said exterior surface to permit electrochemical contact between said electrode and said fluid in said fluid-confining apparatus.

2. The sealing ring of claim 1 wherein said electrode is embedded within said body and is spaced from said exterior surface.

3. The sealing ring of claim 1 wherein said electrode is an electrochemically inert electrode.

4. The sealing ring of claim 1 wherein said electrode is a pH sensitive electrode.

5. The sealing ring of claim 1 wherein said electrode is a specific ion-sensitive electrode.

6. The sealing ring of claim 1 wherein said sealing ring is an O-ring.

7. The sealing ring of claim 1 wherein said channels are slits.

8. The sealing ring of claim 1 wherein said channels are filled with an ionically conducting solid.

9. The sealing ring of claim 8 wherein said ionically conducting solid is an anion exchange resin.

10. The sealing ring of claim 1 wherein said body of said sealing ring is made from nitrile rubber.

11. The sealing ring of claim 1 wherein said body of said sealing ring is made from a silicone elastomer.

12. The sealing ring of claim 1 wherein said body of said sealing ring is made from a partially or completely fluorinated elastomer.

13. The sealing ring of claim 1 comprising a plurality of electrodes.

14. The sealing ring of claim 13 comprising a reference electrode and a counter electrode.

* * * * *